United States Patent [19]

Clark

[11] Patent Number: 4,562,749
[45] Date of Patent: Jan. 7, 1986

[54] SAMPLER

[75] Inventor: Rex K. Clark, Fawley, England

[73] Assignee: Exxon Research and Engineering Co., Florham Park, N.J.

[21] Appl. No.: 416,947

[22] Filed: Sep. 13, 1982

[30] Foreign Application Priority Data

Apr. 2, 1980 [GB] United Kingdom ............. 8011004
Mar. 11, 1981 [GB] United Kingdom ............. 8107670

[51] Int. Cl.$^4$ ............................................. G01N 1/14
[52] U.S. Cl. .................................................. 73/863.84
[58] Field of Search .......... 73/863.82, 863.51, 863.02, 73/863.83, 863.84, 863.86, 863.73, 863.72, 864.64, 864.67, 864.63, 864.33

[56] References Cited

U.S. PATENT DOCUMENTS 3,031,890 5/1962 Struck.

FOREIGN PATENT DOCUMENTS 846589 9/1957 United Kingdom .................. 106/5
1224522 11/1968 United Kingdom.
2108082A 10/1981 United Kingdom.

OTHER PUBLICATIONS

Welker Engineering Company Sampler Style VCM-6BD Description, (2 pages).
Jiskoot Series 200 Grab Sampler brochure, (2 pages).
Welker Engineering Company (5 pages of drawings re GS and LS Style Fluid Samplers).

Primary Examiner—S. Clement Swisher
Attorney, Agent, or Firm—Donald F. Wohlers

[57] ABSTRACT

A fluid pipeline sampler is disclosed which operates so as to trap a liquid sample and then eject it. To achieve this, a piston (18) and sleeve (14) within a casing (1) are displaced together downwardly to move a pair of portholes (10, 11) in the sleeve out of register with a pair of ports (2, 3) in the casing wall, so as to trap the liquid sample in an internal space between the two portholes (10, 11). In this position the sleeve (14) is restrained against further downward movement. On continuing downward advancement of the piston, the trapped liquid sample is ejected out of the internal space through a passageway (21) in the piston for analysis.

14 Claims, 8 Drawing Figures

SAMPLER

BACKGROUND OF THE INVENTION

This invention relates to a sampler for the extraction of fluid samples in flowing or static state.

There is a great need to sample liquid, for example, crude oil under substantially isokinetic conditions. Many devices exists but they do not take representative samples because they do not operate in accordance with isokinetic principles. Some, for example, use complex bypass loops with motor driven circulating pumps. Some lack facilities for possible ejection of the sample and have a longer and complex flow path to the sample receptacles. Others are not bidirectional and others are extremely complex units with many component parts. Some have no facilities for changing the quantity of samples.

For sampling under non-isokinetic conditions, samplers are known which are of relatively simple construction. One such sampler employs a block of rubbery material with a cavity therein in which a liquid sample is trapped by an advancing piston and then expelled through a passage way in the piston as the piston squashes the cavity and the rubbery block flat. However, with sufficiently prolonged use, the rubbery material deteriorates and eventually fails and, in any case, is generally unsuitable for high temperature use which can for example be encountered when sampling North Sea oil. In another sampler, a closed-ended cylinder is used in place of the rubbery block but the hydraulic shock-waves produced when the piston enters the open end of the cylinder, particularly at high sampling rates, can rupture the internal seals and even cause severe internal damage.

Another known sampling device, which is not subject to the disadvantage just mentioned, operates with rotary action to trap a liquid sample in a cylindrical sample cup by rotating a cylindrical sleeve into a first position, and then causing a piston in the sample chamber to eject the trapped sample through a passageway leading from the sample chamber. This sampler, however, suffers from a number of drawbacks, viz., constructional complexity, large bearing surfaces in sliding contact leading to increased wear and risk of jamming caused by dirt, practical sealing difficulties, and limitation on the sampling rate caused by the piston displacement speed during sample expulsion being governed by the line pressure of the pipe line or similar into which the sampler is fitted.

SUMMARY OF THE INVENTION

The present invention is concerned with providing a sampling device which is of simple construction, has a long and trouble free service life, is suitable for high temperature use and can be adapted for isokinetic sampling.

In summary, the invention provides a fluid sampler comprising a casing having two ports in the wall thereof so that the casing can be arranged in communication with a pipeline. One of the ports enables fluid in the pipeline to flow into the sampler and the other port enables fluid in the sampler to flow out of it. A sleeve is reciprocably mounted within the casing and a piston is reciprocably mounted within the sleeve.

Actuator means are provided which are operable for selectively changing the relative positions of the casing, sleeve and piston such that in a first relative position communication is provided through a chamber between the two ports so that the chamber becomes charged with liquid in the pipeline. In a second relative position a sample of the fluid is isolated from the fluid flow within a space bounded by the piston, sleeve and casing. In a third relative position, the volume of the space is reduced for discharging fluid in the space through a passageway in communication with space. This fluid sampler is simple in construction, comprising essentially only three main components, viz., the casing, its sleeve and the piston, these being provided with the actuator means which can be sited at any convenient location. Because none of the components needs to consist of a rubbery material, they can be made of materials such as metal which are resistant to the temperature of hot liquids and can be designed to have a very long service life. Furthermore, because of the reciprocating, as opposed to rotary, action of the sleeve and piston, sliding friction can be reduced, and the likelihood of jamming due to ingress of dirt is lessened. Because both the piston and sleeve have a reciprocating movement, the design of the actuator means is simpler than if it were to have to reciprocate the piston but rotationally oscillate the sleeve. Another advantage over the prior art rotary action sampler where the piston is displaced under the action of line pressure is that because the piston is reciprocated by the action of the actuator means, the sampler can be designed for much higher sampling rates.

Preferably, the sampler is so designed that it can be inserted through an aperture in the pipeline and suspended there so that fluid can flow into one port and can also flow out through the other port. This arrangement makes the fluid sampler especially suitable for sampling oil flowing in an oil pipeline.

In one convenient arrangement, a compression spring, located between the piston sleeve and a shoulder, formed within the casing, and acting as its lower end on a top part of the sleeve, is provided for biasing the sleeve towards a position in which the fluid sample is isolated within said space, the spring being in its state of greatest compression when the casing, sleeve and the piston are in their first relative positions. This arrangement is compact and utilises the spring force to assist in rapidly displacing the sleeve relative to the casing during changeover of the relative positions of the casing, sleeve and piston away from the first relative position.

Suitably the casing, sleeve and piston are of circular cross-section and the two ports are diametrically opposite one another. This assists in providing simplicity of manufacture and assembly and linear flow of liquid in the pipeline through the fluid sampler.

For achieving isokinetic flow conditions, the shape and design of the ports and the chamber are chosen so that the flow through the fluid sampler, when the casing, sleeve and piston are in their first relative position, is substantially isokinetic. This can be achieved in a fluid sampler in which the casing and piston provide flat surfaces which are substantially at right angles to the longitudinal axis of the sleeve and define opposite walls of the chamber when the casing, sleeve and piston are in their first relative position, the planes of the flat surfaces lining up with the ports at the perimeters thereof such that fluid flowing through one port and out through the other port has a substantially uninterrupted path and without there being substantially any cavities to create dead fluid flow areas in the chamber.

In one particular arrangement, both for isokinetic and non-isokinetic sampling, the wall of the sleeve is formed with two portholes which align one with each of the two ports when the casing, sleeve and piston are in their first relative position, each port is the same size as the porthole with which it registers, and the arrangement of the sleeve and piston is such that they are moved together by the actuator means relative to the casing during the changeover from the first to the second relative positions of the casing, sleeve and piston but the piston alone is moved further, in the longitudinal direction of the sleeve, during changeover from the second to the third relative positions. This arrangement is advantageous in that it merely requires the actuator means to take the form of a double-acting actuator and a lost-motion device which becomes operative after the sleeve has been arrested in the second relative position of the casing, sleeve and piston. To assist in achieving isokinetic sampling with such a sampler, the sleeve can be made cylindrical and the chamber bounded by two transverse flat circular surfaces defined by the bottom end of the piston and by the upper end surface of the plug sealing the end of the sleeve. Preferably these flat surfaces lie respectively in the planes of the upper and lower extremities of the portholes in the first and second relative positions of the sampler.

The sleeve may include a plug mounted in the bottom region of the sleeve and having a flat surface constituting a boundary wall of the chamber. The plug is advantageous in that it can be removed for enabling the interior of the chamber and the neighbouring internal regions to be inspected.

A stop can be provided for arresting the sleeve from further movement in the same direction after arriving in the second relative position of the casing, sleeve and piston from the first relative position. The stop constitutes a simple and effective way of arresting the motion of the sleeve.

One way of handling and collecting the sample ejected from the chamber is for the said passageway to be formed in the piston and the piston provided with a piston rod which extends to the inner sleeve, the passageway being extended to pass within the piston rod in the longitudinal direction thereof and communicating via a flexible tube or pipe with a receptacle for receiving fluid discharged from the sampler.

One preferred embodiment, which is specially designed for isokinetic sampling, comprises a casing having two ports in the wall thereof, the casing being capable in communication with the pipeline so that fluid in the pipeline can flow into one port and out of the other port, the axis of the pipeline being substantially at right angles to the axis of the casing. A sleeve is reciprocatable within the casing and is provided with two portholes capable of aligning with the ports in the casing, each porthole being substantially no greater in size than its adjacent port. The sleeve has a chamber formed therein, at least when the ports and portholes are aligned, the boundary of the chamber comprising a pair of walls, the planes of which are substantially at right angles to the longitudinal axis of the sleeve and which when the portholes are aligned with the ports of the casing meet at the portholes at the perimeters thereof so that fluid flowing through one aligned port and porthole and out through the other aligned porthole and port has a substantially uninterrupted path and without there being substantially and cavities in the chamber.

Finally, means are provided for removing from the chamber fluid which has been collected there.

In using the sampler the sleeve is raised or lowered so that both ports and portholes are aligned. At this stage fluid is flowing through the sampler, entering through one port of the casing and leaving by the other port. This flow is at constant velocity and at the same velocity as the flow of fluid passing around the casing. Thereafter, the sleeve is shifted so that there is no longer any passage of fluid through the sampler i.e., the ports in the casing are blocked by the walls of the sleeve. A sample of fluid is therefore trapped in the chamber and it can be removed from this chamber by the means provided and it can then be analysed, if desired.

In its simplest form the casing and sleeve are of circular cross-section and the ports and portholes are circular or oval. Usually the ports and portholes are diametrically opposite one another. There should be means to prevent relative rotation of the casing and the sleeve so as to prevent the possibility that the ports and portholes are misaligned radially. One such means comprises a protrusion in the casing mating with a longitudinal channel in the sleeve. Alternatively the casing can have a longitudinal slot or channel and the casing can have a protrusion.

It is especially convenient if the sleeve is cylindrical and the chamber formed by two transverse circular plates fixed to the inside of the sleeve and meeting the inner surface of the sleeve at the extremities of the portholes, i.e., tangentially. In this manner, there is no spread of the fluid in the longitudinal direction of the sleeve as the fluid flows straight through the chamber in a direction which is at right angles to the longitudinal axis of the casing and sleeve. Also the fluid has an uninterrupted flow through the casing and sleeve. Finally there are the means for removing from the chamber fluid which has been collected in the chamber. The simplest form would be a tap in the bottom of the chamber which could be shut when the chamber is being used to collect fluid and opened when fluid no longer flows into the chamber and it is desired to collect the fluid.

Although the above briefly described sampler can be used for various applications, in practice it has been found necessary to use a rather more sophisticated design of sampler. Accordingly such a fluid sampler comprises a casing having a stop on the internal surface thereof and having two ports in the wall thereof, the casing being capable of being in communication with the pipeline so that fluid in the pipeline can flow into one port and out of the other port, the axis of the pipeline being substantially at right angles to the axis of the casing, the piston sleeve having a base and in slidable contact with the inner surface of said casing and having portholes therein adjacent to the base thereof capable of aligning with the ports of the casing, each porthole being substantially no greater in size than its aligned port, a piston in slidable contact with the inner surface of said sleeve movable therein from a position just clear of the portholes, past the portholes to a position in contact with the base (i.e. seal plug 9) of the sleeve, a piston having a passageway therein extending the length thereof, and resilient means enabling pressure on the piston to move the sleeve and piston past the ports in the casing until the base of the piston sleeves contacts the stop of the casing when further pressure on the piston forces the piston into contact with the base of the piston sleeve.

When depressing the piston and sleeve in using the preferred sampler of the invention, the ports of the casing are closed by the piston sleeve and a sample of fluid is isolated in the volume bounded by the base of the piston sleeve, the inner surface of the casing and the lower end of the piston. On further depressing the piston so that it contacts the base of the piston sleeve the fluid is forced up through the passageway in the piston when it can be collected in a receptacle. In this manner only a single downward short stroke is required.

It is preferred but not essential that the casing, sleeve and piston are circular in cross-section. This form is cheaper to make and less likely to result in jamming than if the cross-section were square or rectangular. However, when the cross-section is circular there are means to ensure that there is no relative rotation between the sleeve and the casing so that the ports and portholes can always be aligned by shifting the sleeve relative to the casing along their longitudinal axis. Generally a mating longitudinal channel and protrusion achieves this result.

Generally the casing should be elongate, i.e., be of a length considerably greater than its diameter if cylindrical or its greatest cross-sectional dimension if not circular in cross section.

The two ports are usually near but not at the end of the casing so that there is space for the sleeve to be depressed so as to close the ports in the casing. The casing has a stop on the internal wall thereof so as to prevent the piston sleeve from sliding past the end of the casing and to enable further pressure on the piston to force the piston into contact with the base of the piston sleeve. This stop can be any lug or internal protrusion, preferably at least two, but the most preferred stop is a seat collar, the outer dimensions of which are substantially the same as the internal dimensions of the casing. A particularly preferred form when the casing is cylindrical is a collar with an external screw thread capable of screwing into the base of the casing. It is essential that the stop does not close the end of the casing completely because it is necessary to permit displacement of any fluid trapped below the base of the piston sleeve when the piston sleeve descends. Hence a seat collar is particularly suitable.

The two ports are preferably aligned i.e., diametrically opposite one another if the casing is cylindrical. However this is not absolutely necessary and the ports could be located so that they co-operate with two ends of a pipeline which are at right angles to one another. It is particularly desirable however that the axis of the pipeline is substantially at right angles to the axis of the casing, the axis of the casing being the direction in which piston and piston sleeve reciprocate.

If desired each port can be provided with a flange so that they can be bolted to flanges on the ends of the pipeline. Preferably a seal is interposed between the flange on a port and on the pipeline.

It is preferred however for the sampler to be designed so that it can be inserted through an aperture in the pipeline and suspended in the pipeline so that fluid can flow through one port and out through the other port. This can be achieved by fixing a socket to the aperture, the inner surface of the socket having a screw thread. The upper portion of the casing of the sampler can be provided with a screw thread which co-operates with that of the socket. Alternatively the upper end of the sampler can screw into a block, the upper end of the block having the yoke of a pneumatic actuator attached thereto.

The piston sleeve must be capable of sliding within the casing and there should be only the minimum gap between the outer surface of the sleeve and the inner surface of the casing. The sleeve serves as a valve to block the ports of the casing and at the same time trap a sample of fluid flowing through the pipeline.

There are portholes in the sleeve designed to be capable of aligning or registering with the ports in the casing. This alignment is achieved by shifting the sleeve longitudinally within the casing until the ports and portholes are level with each other. Each porthole should preferably be the same size as the port with which it registers. Preferably all portholes and ports should be oval, the longer axis being transverse to the longitudinal axes of the sleeve and casing. Less desirably the ports and portholes are circular, square or rectangular.

The lower end of the sleeve is provided with a base. Preferably this is achieved by threading internally the lower end of the sleeve and fitting it with a sealing plug.

Slideable within the piston sleeve is a piston. There is preferably also a piston rod also having a passageway extending the length thereof. Preferably the piston sleeve is provided with an end section opposite the base thereof so that this piston rod can pass through an aperture in the top end section of the piston sleeve. In order to equalise pressure piston sleeves with end members should be provided with one or more apertures, these preferably being located in the member itself.

The passageway within the piston (and piston rod) and extending the length thereof is preferably located centrally of the cross-section of the piston i.e. along the axis when casing, piston sleeve and piston have circular cross-section. The purpose of this passageway is to allow the sample of fluid to be forced out of the sampler when the piston is forced into contact with the base of the sleeve.

The passageway in the piston or piston rod is preferably provided with a non-return valve for example ball and spring so that there is no flow of the fluid being sampled passing to a receptacle or drain back of sample fluid from a receptacle when the sampler is not being used.

The resilient means are preferably a compression spring which may be located between the piston sleeve and a shoulder formed on the piston rod or a shoulder formed within the casing. The shoulder formed on the piston rod if of the same diameter as the inner diameter of the casing can also act as a guide disc for the piston rod. If the shoulder formed on the piston rod is in slideable contact with the interior of the casing then it should be provided with one or more apertures so as to equalise the pressure both sides of the shoulder.

The passageway should communicate with a receptacle for the sample. Since the piston moves, the connecting tube or pipe between the passageway and receptacle will usually be flexible. Alternatively it is possible to have an elongated aperture from the passageway in communication with the connecting tube or pipe such that with the further movement of the piston after the piston sleeve has contacted the closed end there is still communication between the passageway and said tube or pipe.

To obtain a sample from fluid flowing in a pipeline after the sampler has been positioned in the pipeline with the portholes of the sleeve aligned with the ports of the casing, pressure is exerted on the piston via the piston rod. This forces down the piston and piston sleeve, the latter closing the ports of the casing, the piston sleeve eventually contacting the stop of the casing. Further pressure on the piston forces the piston down further until it contacts the base of the piston sleeve. At the same time the sample of fluid originally trapped within the confines of the piston sleeve is forced out of the sampler through the passageway within the piston and piston rod.

Usually the fluid will be a liquid, for example oil, but it can be a gas. In the case where gases are sampled it is preferred that the wall of the piston be provided with an "O-ring" seal so that there is no leakage between the piston and piston sleeve and also for "O-ring" seals to be provided between the piston rod and sleeve to prevent leakage near the outlet from the passageway to the tube or pipe connected to the receptacle. In fact the presence of an O-ring seal could be desirable even when sampling liquids.

The sampler may be operated by a relatively simple control system involving the use of compressed air, a diaphragm and solenoid valves as will be described later.

The advantages of the sampler are manifold. It can ensure that it operates in accordance with isokinetic principles and there are very few moving parts or small complex components. There is unlimited compression power for positive injection. Also there is bi-directional operation, and the quantity of sample may be adjusted on-line. Furthermore the sampler may be easily coupled to a simple pneumatic pulse integrator to log the number of samples taken.

DESCRIPTION OF THE DRAWINGS

A preferred form of the fluid sampler of the invention is now described, by way of example, with reference to the drawings in which.

DETAILED DESCRIPTION OF THE INVENTION

Figure 1:
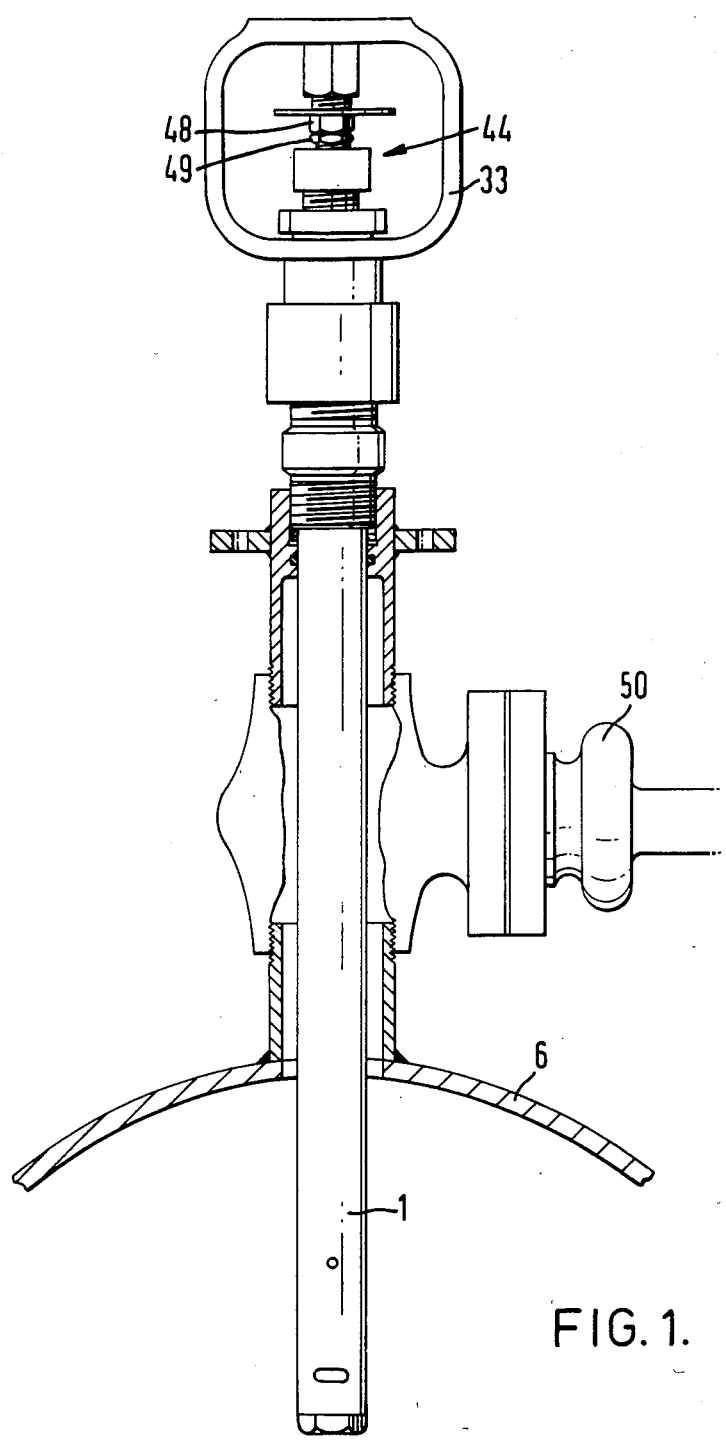
FIG. 1 shows a view in part section, of the top portion of a sampler.
Figure 2:
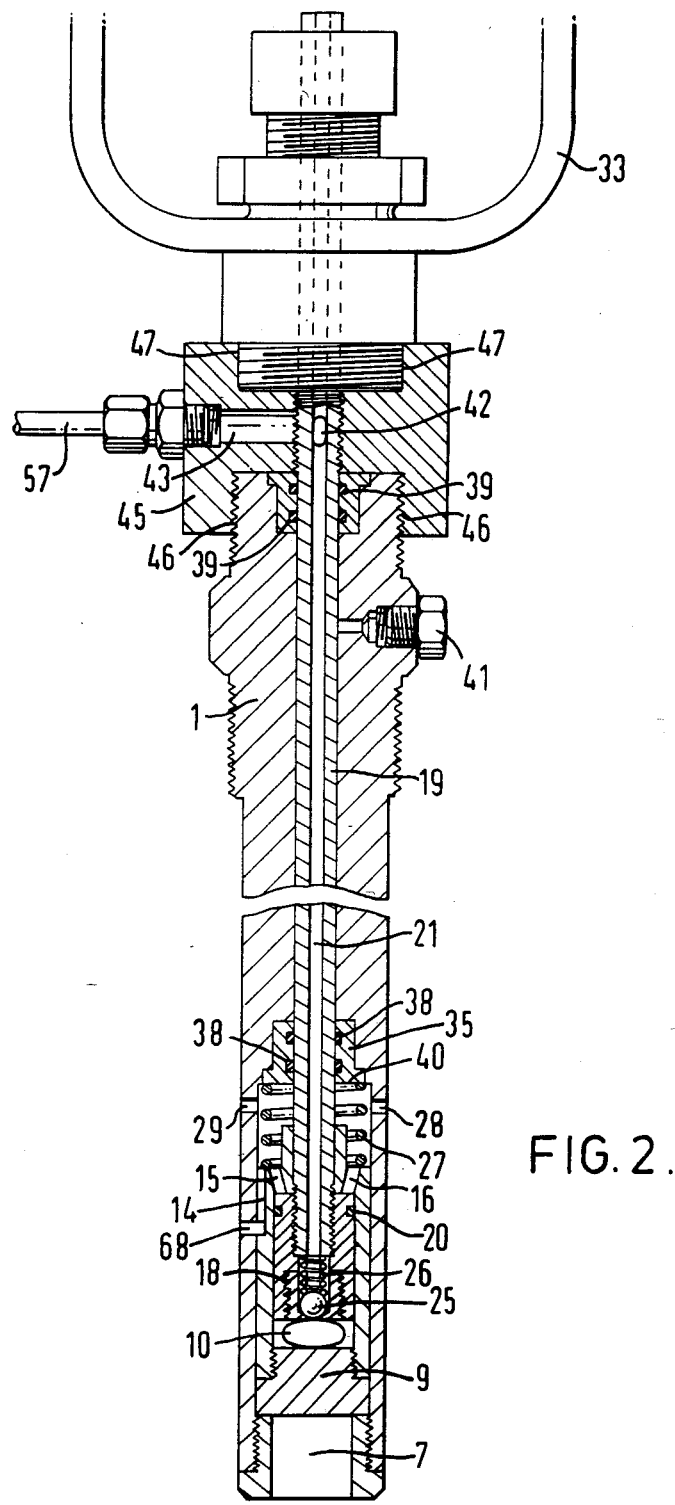
FIG. 2 shows a section through the bottom portion of the sampler of FIG. 1.

Referring to FIGS. 1 to 5 the clindrical casing 1 is provided with two oval ports 2 and 3. The casing 1 is provided with a seat ring 7 screwed into the bottom thereof.

Slideable within casing 1 is the piston sleeve 14, the lower end of which is internally threaded and fitted with a sealing plug 9. The sleeve 14 has two apertures 15 and 16 and to equalise pressure each side of the sleeve and a central aperture 17 to accommodate the piston rod 19. The sleeve 14 also has two diametrically opposed oval portholes 10 and 11 the same size as the ports 2 and 3 and capable of registering therewith. Relative rotation betwen casing 1 and sleeve 14 is prevented by a protrusion pin 68 communicating with a longitudinal channel in sleeve 14.

The piston 18 into which piston rod 19 is screwed is provided with an O-ring seal 20 and an axially located passageway 21 which extends the length of the piston 18 and piston rod 19. There are O-ring seals 38 making a fluid-tight seal when the piston rod slides in the block 35 forming a shoulder 40.

Located within the passageway 21 is a non-return valve comprising a ball 25 and a compression spring 26. Between the top of the piston sleeve 14 and the shoulder 40 formed in the casing 1 is a compression spring 27. Apertures 28 and 29 are for equalising pressure.

Further up the casing there is an inspection plug 41 and there are also some further O-ring seals 39 at the top of the casing. Surmounting the casing 1 is a sampler transfer block 45 which is screwed onto casing 1 by means of screw thread 46. A standard pneumatic actuator (including yoke 33) is indicated in FIG. 1 generally as 44 and is screwed into sampler transfer block 46 by thread 47.

There is also an isolation valve 50 whereby when the sampler is removed from the pipeline 6 the aperture at the top of the pipeline can be sealed off.

The sample of fluid which is collected emerges from the top of the passageway 21 by means of an elongated aperture 42 which is always in communication with conduit 43 which is connected to pipe-line 57.

Leakage of fluid in transferring from passageway 21 to conduit 43 is prevented by the O-ring seals 39.

The stroke adjustment whereby the volume of sample can be altered is by means of the nuts 48 and 49 indicated in FIG. 1.

Figure 5:
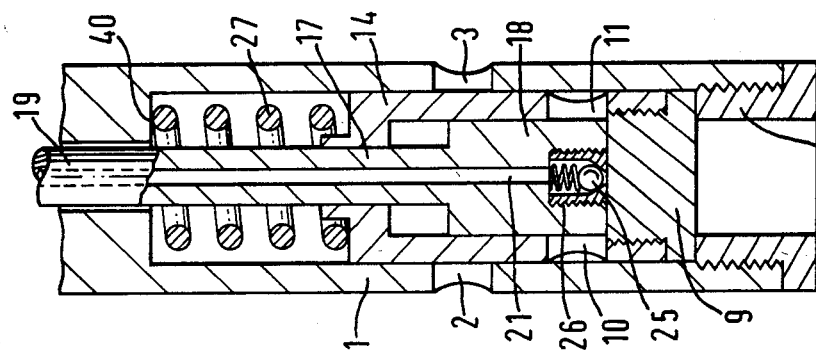
FIGS. 3 to 5 show diagrammatically the various positions of the piston and piston sleeve within the casing as the piston and piston sleeve are depressed.
Figure 4:
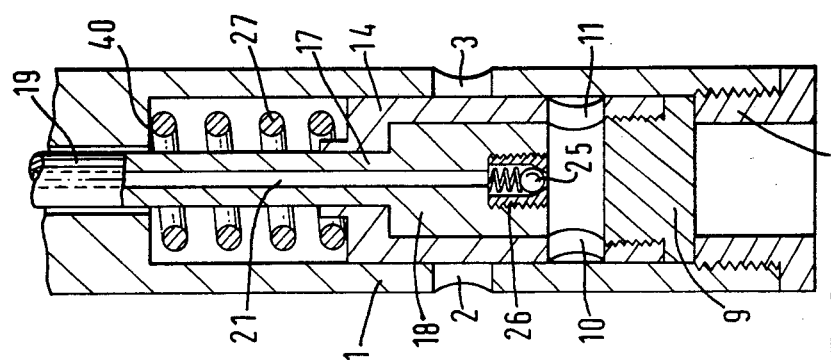
Figure 3:
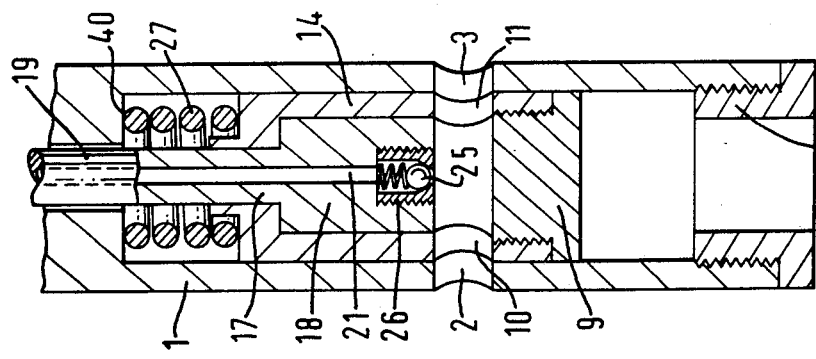

Referring to FIGS. 3 to 5 to obtain a sample it is necessary to move the piston 18 and piston sleeve 14 upwards so that the portholes 10 and 11 register with the ports 2 and 3, respectively, as shown in FIG. 3.

The presence of the compression spring 27 located between the shoulder 40 and the top of piston sleeve 14 means that when the piston rod 19 is moved upwards, both piston 18 and sleeve 14 ascend together. Likewise when the piston rod 19 is depressed both piston 18 and sleeve 14 descend together. Thereafter it is necessary to exert further force, forcing down the piston 18 and piston sleeve 14 until the sealing plug 9 of the latter contacts the seat ring 7 of the casing 1 as shown in FIG. 4.

The sample is trapped between the bottom of the piston 18 and the plug 9 of the piston sleeve 14. Further pressure on the piston rod 19 results in the piston 18 being forced down into contact with the plug 9 of the sleeve 14 as shown in FIG. 5, thereby forcing the sample up the passageway 21, through aperture 42, conduit 43, pipe-line 57 and to the sample receptacle.

Figure 6:
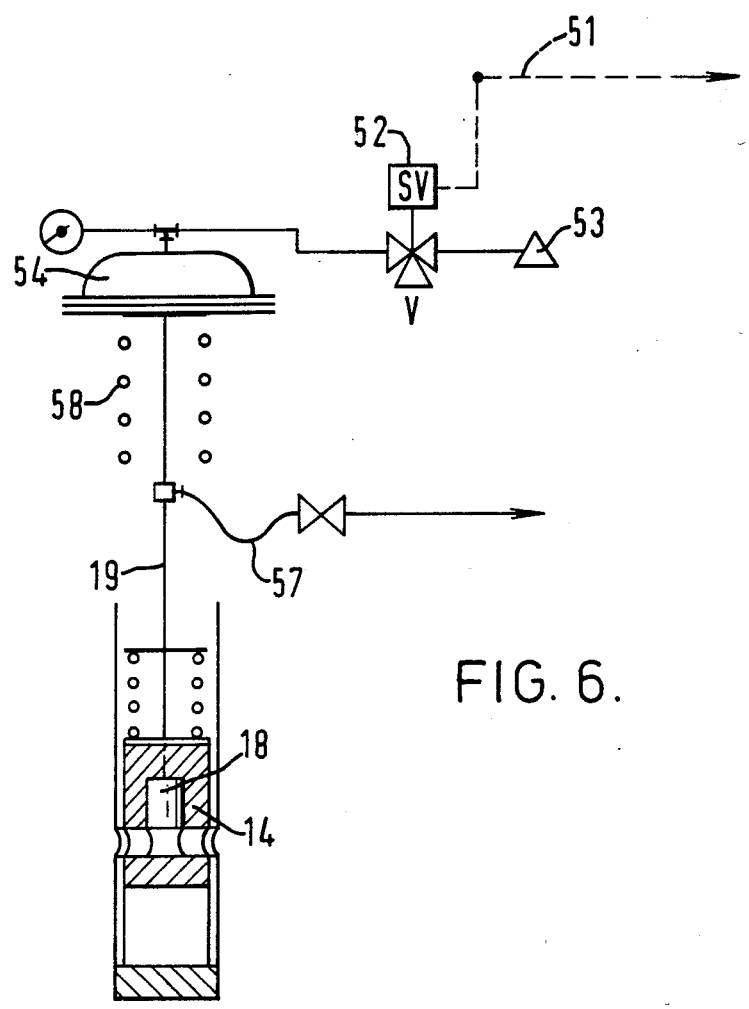
FIGS. 6 to 8 show the sequence of operations wherein the sample of fluid is automatically collected from a pipeline and discharged from the sampler of FIGS. 1 to 5.

Referring now to FIG. 6 a signal from controlling elements via a short time delay unit (not shown) connected to line 51 immediately energises solenoid 52. This energising of the solenoid 52 causes supply air from reservoir 53 to pass to the diaphragm 54, this diaphragm 54 and a compression spring 58 forming part of a standard pneumatic actuator. Since this diaphragm 54 is pressurised this causes the piston rod 19, piston 18 and piston sleeve 14 to move downwards together, compressing compression spring 58.

Figure 7:
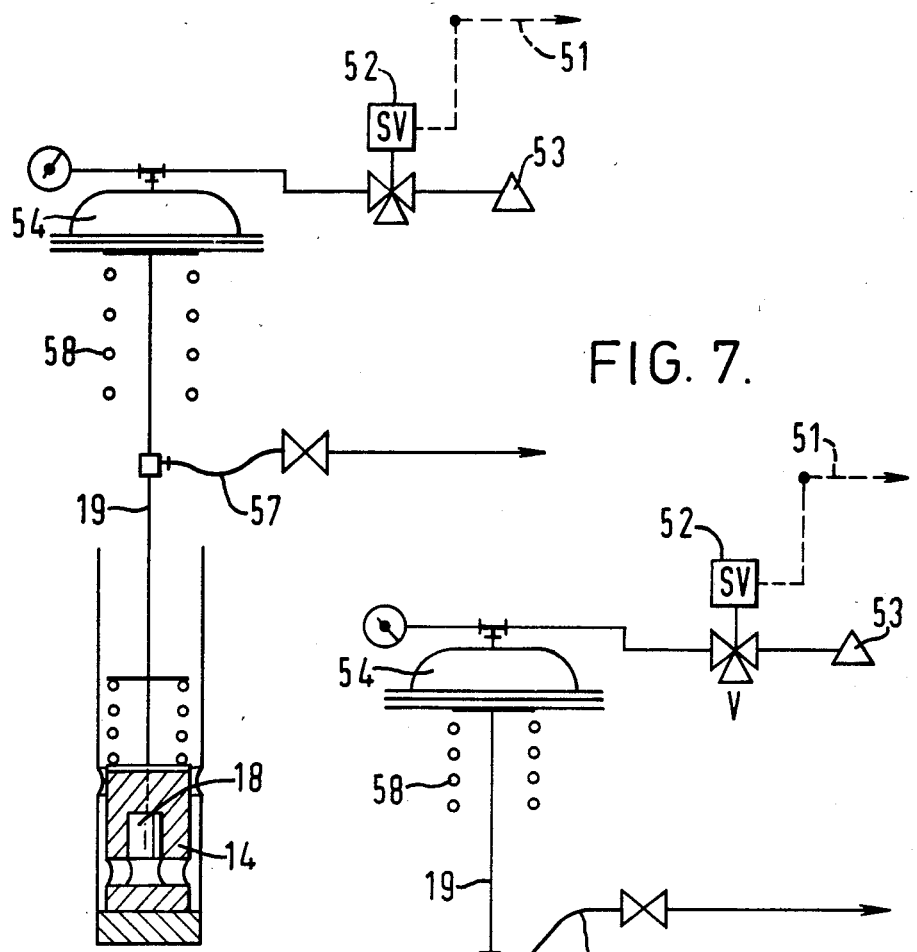

Referring to FIG. 7 when the pressure in the diaphragm 54 reaches the region of 0.85 kg/cm$^2$ the sealing plug 9 of the sleeve 14 will be firmly seated on the seat ring 7 of the casing 1, the sleeve holding the captive sample.

Figure 8:
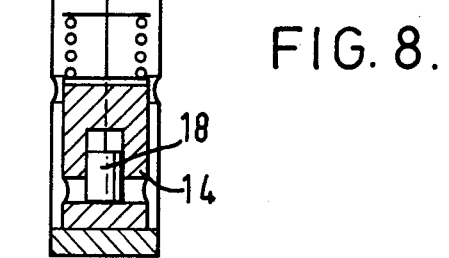

Referring to FIG. 8 as the pressure of the diaphragm 54 rises the piston 18 is now driven downwards, compressing the fluid and transferring it through line 57 to the sample receptacle.

Just as full air pressure is applied to the diaphragm 54 the short time delay unit has come to the end of the time cycle and the electrical signal is removed from the solenoid valve 52. The de-energising of the solenoid 52 vents the air from diaphragm 54 via the vent (V) on the solenoid valve 52 and the compression spring 58 causes the piston rod 19, piston 18 and piston sleeve 14 to move upward.

I claim:

1. A fluid sampler comprising a casing having two ports in the wall thereof so that the casing can be arranged in communication with a pipeline, one of the ports enabling fluid in the pipeline to flow into the sampler and the other port enabling fluid in the sampler to flow out of it, a sample isolating sleeve reciprocably mounted within the casing, a sample ejecting piston reciprocably mounted within the sleeve, and actuator means operable for selectively changing the relative axial positions of the casing, sleeve and piston such that in a first relative axial position, the sleeve allows communication between the two ports, in a second relative axial position the sleeve cuts off communication between the two ports and thereby isolates a sample of the fluid from the fluid flow within an internal space bounded by the piston, sleeve and casing, and in a third relative position the volume of said space is reduced for forcibly discharging fluid in said space from the fluid sampler through a passageway in communication with said space.

2. A fluid sampler according to claim 1, which is so designed that it can be inserted through an aperture in the pipeline and suspended in the pipeline so that fluid can flow into one port and can also flow out through the other port.

3. A fluid sampler according to claim 1, wherein a compression spring, which is located between said sleeve and a shoulder, formed within said casing, and acts at its lower end on a top part of said sleeve, is provided for biasing the sleeve towards a position in which the fluid sample is isolated within said space, the spring being in its state of greatest compression when the casing, sleeve and piston are in their first relative position.

4. A fluid sampler according to claim 1, wherein said casing, sleeve and piston are of circular cross-section and the two ports are diametrically opposite one another.

5. A fluid sampler according to claim 1, wherein the casing and piston provide flat surfaces which are substantially at right angles to the longitudinal axis of the sleeve and define opposite walls of said chamber when the casing, sleeve and piston are in their first relative position, the planes of said flat surfaces lining up with the ports at the perimeters thereof such that fluid flowing through one port and out through the other port has a substantially uninterrupted path and without there being substantially any cavities in the chamber.

6. A fluid sampler according to claim 1, wherein the shape and design of said ports and said chamber is such that the flow through the fluid sampler, when the casing, sleeve and piston are in their first relative position, is substantially isokinetic.

7. A fluid sampler according to claim 1, wherein the wall of the sleeve is formed with two portholes which align one with each of said two ports when the casing, sleeve and piston are in their first relative position, each port is the same size as the porthole with which it registers, and the arrangement of the sleeve and piston is such that they are moved together by the actuator means relative to the casing during the changeover from the first to the second relative positions of the casing, sleeve and piston, but the piston alone is moved further, in the longitudinal direction of the sleeve, during changeover from the second to the third relative position.

8. A fluid sampler according to claim 1, wherein the sleeve includes a plug mounted in the bottom region of the sleeve and having a flat surface constituting a boundary wall of said internal space.

9. A fluid sampler according to claim 1, wherein a stop is provided for arresting the sleeve from further movement in the same direction after arriving in the second relative position of the casing, sleeve and piston from the first relative position.

10. A fluid sampler according to claim 1, wherein said passageway is formed in the piston and the piston is provided with a piston rod which extends within the sleeve, said passageway being extended to pass within the piston rod in the longitudinal direction thereof and communicating via a flexible tube or pipe with a receptacle for receiving fluid discharged from the sampler.

11. A fluid sampler comprising a casing having two ports in the wall thereof, the casing being capable of being in communication with a pipeline so that fluid in the pipeline can flow into one port and out of the other port, the axis of the pipeline being substantially at right angles to the axis of the casing, a sleeve reciprocatable within the casing provided with two portholes capable of aligning with the ports in the casing, each porthole being substantially no greater in size than its adjacent port, said sleeve having a chamber formed therein, at least when said ports and portholes are aligned, the boundary of the chamber comprising a pair of walls, the planes of which are substantially at right angles to the longitudinal axis of the sleeve and which when the portholes are aligned with the ports of the casing, meet the portholes at the perimeters thereof so that fluid flowing through one aligned port and porthole and out through the other aligned porthole and port has a substantially uninterrupted path and without there being substantially any cavities to create dead fluid flow areas in the chamber, and means for removing from the chamber fluid which has been collected in the chamber.

12. A fluid sampler comprising a casing having a stop on the internal surface thereof and having two ports in the walls thereof, the casing being capable of being in communication with a pipeline so that fluid in the pipeline can flow into one port and out of the other port, the axis of the pipeline being substantially at right angles to the axis of the casing, a sleeve having a base and in slideable contact with the inner surface of said casing and having portholes therein adjacent to the base thereof capable of aligning with the ports of the casing, each porthole being substantially no greater in size than its aligned port, a reciprocating piston in slideable contact with the inner surface of said sleeve movable therein from a position just clear of the portholes, past the portholes to a position in contact with the base of the sleeve, the piston having a passageway therein extending the length thereof and resilient means enabling pressure on the piston to move the sleeve and piston past the ports in the casing until the base of the sleeve contacts the stop of the casing when further pressure on the piston forces the piston into contact with the base of the sleeve.

13. A sampler according to claim 12 wherein the piston has an end section opposite the base thereof and the piston is connected to a piston rod having a passageway therein extending the length thereof and in communication with the passageway in the piston, said piston rod passing through an aperture in the end section of the sleeve.

14. A sampler according to claim 12, wherein the passageway in the piston rod terminates in an elongated aperture which throughout the stroke of the piston is always in communication with a conduit capable of being connected to a receptacle for the sample.

* * * * *